United States Patent
Kaytor et al.

(10) Patent No.: US 10,220,018 B2
(45) Date of Patent: *Mar. 5, 2019

(54) METHOD OF MITIGATING LONG AND SHORT TERM DETRIMENTAL EFFECTS OF EXPOSURE TO LOW DOSE IONIZING RADIATION BY ADMINISTRATION OF GENISTEIN

(71) Applicant: Humanetics Corporation, Edina, MN (US)

(72) Inventors: Michael D. Kaytor, Maplewood, MN (US); John L. Zenk, Eden Prairie, MN (US)

(73) Assignee: Humanetics Corporation, Edina, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/977,023

(22) Filed: May 11, 2018

(65) Prior Publication Data
US 2018/0256535 A1    Sep. 13, 2018

Related U.S. Application Data

(60) Continuation of application No. 15/450,628, filed on Mar. 6, 2017, now Pat. No. 9,993,455, which is a division of application No. 13/856,909, filed on Apr. 4, 2013, now Pat. No. 9,623,003.

(51) Int. Cl.
| | |
|---|---|
| *A61K 31/352* | (2006.01) |
| *A61K 9/00* | (2006.01) |
| *A61K 9/14* | (2006.01) |
| *A61K 31/353* | (2006.01) |

(52) U.S. Cl.
CPC .......... *A61K 31/352* (2013.01); *A61K 9/0053* (2013.01); *A61K 9/14* (2013.01); *A61K 31/353* (2013.01)

(58) Field of Classification Search
USPC ........................................................ 514/353
See application file for complete search history.

*Primary Examiner* — Kathrien A Cruz
(74) *Attorney, Agent, or Firm* — Sherrill Law Offices, PLLC

(57) ABSTRACT

Mitigation of long and short-term detrimental effects of exposure to low dose ionizing radiation by administration of genistein in the form of a nanosuspension to a mammal in an amount effective for achieving genistein serum levels of between 1-5 µM in the mammal throughout a time period from exposure to the ionizing radiation to twelve hours after exposure to the ionizing radiation.

8 Claims, No Drawings

METHOD OF MITIGATING LONG AND SHORT TERM DETRIMENTAL EFFECTS OF EXPOSURE TO LOW DOSE IONIZING RADIATION BY ADMINISTRATION OF GENISTEIN

FIELD OF INVENTION

The invention relates to methods of mitigating the formation of or promoting the repair of biological damage following low dose radiation exposure.

BACKGROUND

Each year an individual is exposed to approximately 6.2 mSv of ionizing radiation, half of which comes from medical diagnostic procedures. In addition to the standard hospital-based diagnostic radiation equipment such as x-ray machines, computed tomography (CT) scanners, positron emission tomography (PET) and nuclear medicine procedures, new ionizing radiation based diagnostic centers for heart scan, virtual colonoscopy and whole-body scan are opening at a rapid rate throughout the world, especially in the United States.

A computed tomography (CT) scan uses ionizing radiation to generate 3D views of internal organs and structures within the body. This form of medical imaging is primarily used to assist in the diagnosis of both acute and chronic medical conditions. The use of CT scans has increased rapidly over the last decade. In 2006 it was estimated that nearly 70 million CT scans were obtained in the US, as compared with approximately 3 million in 1980. The number of CT prescribed scans continues to rise, with 100 million annual scans projected in the US by 2015.

A typical CT scan generates a skin dose in the range of 10-50 mGy. Absorbed doses from multiple CT scans can reach levels that have been shown to induce a low rate of cancer incidence. In the case of CT angiography, typical organ doses from a single CT scan range from 10-25 mGy to as high as 100 mGy to the heart and lung. The rate per capita of CT scan usage in the United States has been estimated to be approximately 220 scans annually per 1000 population, which on a per capita basis is second only to Japan in the developed world. A rise in implementation along with cumulative effects from multiple CT scans brings risks from increased exposure to ionizing radiation.

Ionizing radiation causes DNA double strand breaks. Improper or inefficient repair of these harmful insults can result in an increased risk of birth defects in the event the individual is pregnant at the time of exposure, and development of cataracts and/or cancer later in life. Estimates have suggested that the risk of a fatal cancer occurrence from a single CT scan is about 1 in 500 for children and 1 in 2000 for adults. This is further compounded by increased usage of CT scan procedures, potentially increasing the burden on future health care systems.

Of significant concern is the rise in the use of CT scans in pediatric patients, who are at greater risk for developing cancer throughout their lifetime due to diagnostic or treatment-related exposure to radiation during childhood. One analysis found a 92% increase in CT scans of the abdomen and pelvis performed on children under the age of 15 between 1996 and 1999. Brenner, D., Elliston, C., Hall, E. and Berdon, W. (2001) *Estimated Risks of Radiation-Induced Fatal Cancer from Pediatric CT. AJR. American Journal of Roentgenology,* 176, 289-296.

Children are not only more sensitive to the effects of radiation but also have a longer life expectancy, the combination of which further increases their risk of cancer in adult life. One retrospective study found that in children receiving CT scans, a cumulative dose of about 50 mGy has the potential to almost triple the risk of leukemia and doses of about 60 mGy may triple the risk of brain cancer. Pearce, M. S., Salotti, J. A., Little, M. P., McHugh, K., Lee, C., Kim, K. P., Howe, N. L., Ronckers, C. M., Rajaraman, P., Sir Craft, A. W. et al. (2012) *Radiation Exposure from CT Scans in Childhood and Subsequent Risk of Leukaemia and Brain Tumours: a Retrospective Cohort Study. Lancet,* 380, 499-505.

Not only are cells directly in the path of ionizing radiation at risk, surrounding cells are also affected by radiation exposure. The "radiation-induced bystander effect" has significant implications for low-dose radiation exposure. In one study, a majority of the bystander cells (40-60%) were found to have DNA double strand breaks. Sedelnikova, O. A., Nakamura, A., Kovalchuk, O., Koturbash, I., Mitchell, S. A., Marino, S. A., Brenner, D. J. and Bonner, W. M. (2007) *DNA Double-Strand Breaks Form in Bystander Cells after Microbeam Irradiation of Three-Dimensional Human Tissue Models. Cancer Research,* 67, 4295-4302. These direct and indirect biological effects of low-dose radiation are of significance when assessing total cancer risk. In addition, one group found the number of DNA double-strand breaks measured in blood lymphocytes following CT scan examination to be directly related to the dose-length product. Lobrich, M., Rief, N., Kuhne, M., Heckmann, M., Fleckenstein, J., Rube, C. and Uder, M. (2005) *In Vivo Formation and Repair of DNA Double-Strand Breaks After Computed Tomography Examinations. Proceedings of the National Academy of Sciences of the United States of America,* 102, 8984-8989. These data suggest that efficient means to resolve DNA double strand breaks and other biological damage in cells directly exposed to radiation and more importantly in bystander cells are of importance to mitigate biological-related deleterious effects.

Accordingly, a substantial need exists for a cost-effective method of reducing the detrimental effects of low dose radiation exposure.

SUMMARY OF THE INVENTION

The invention is directed to a method for mitigating at least one of long-term and short-term detrimental effects of exposure to medical imaging ionizing radiation. The method includes the step of administering an effective amount of genistein in the form of a nanosuspension to a mammal within forty eight hours prior to and/or within twelve hours after exposure to medical imaging ionizing radiation.

A specific long-term detrimental effect mitigated by such administration of genestein is cancer. Specific short-term detrimental effects mitigated by such administration of genestein are DNA double strand breaks, as measured in accordance with the procedure set forth in Redon, C. E., Dickey, J. S., Bonner, W. M. and Sedelnikova, O. A. (2009) γ-*H2AX as a biomarker of DNA damage induced by ionizing radiation in human peripheral blood lymphocytes and artificial skin. Adv Space Res.* 43(8): 1171-1178, and an increase in 8-hydroxy-2'-deoxyguanosine levels, as measured in accordance with the procedure set forth in Wang, C. J., Yang, N. H., Chang, C. C., Liou, S. H., Lee H. L. (2011) *Rapid and simple one-step membrane extraction for the determination of 8-hydroxy-2'-deoxyguanosine in human plasma by a* combination of on-line solid phase extraction and LC-MS/MS. *J. Chromatogr B*, 879, 3538-3543.

DETAILED DESCRIPTION OF A PREFERRED EMBODIMENT

Theory

The immediate biological effects from ionizing radiation occur largely due to the DNA damaging effects of hydroxyl radicals produced during radiolytic hydrolysis of water and activation of oxidant generating enzymes that lead to a perpetual state of oxidative stress and free-radical damage to cellular macromolecules. At micromolar concentrations, genistein has potent antioxidant and anti-inflammatory activity and can inhibit protein tyrosine kinase activity, which modulates signal transduction pathways involved in cell death and survival. Without intending to be limited thereby, it is believed that genistein's ability to reduce the detrimental effects of low dose radiation exposure are mediated via genistein's ability to scavenge reactive oxygen species which are directly implicated in the formation of DNA double strand breaks.

Definitions

As utilized herein, including the claims, the term "medical imaging" means creating an image of the body or parts and function thereof for clinical purposes (e.g., medical procedures seeking to reveal, diagnose or examine a disease or disorder) or medical science (e.g., study of normal anatomy and physiology).

As utilized herein, including the claims, the term "medical imaging ionizing radiation" means a single dose of ionizing radiation of less than 100 mGy, intentionally administered for diagnostic purposes to the specific exclusion of administration for therapeutic purposes.

DESCRIPTION

Administration of genistein prior to and/or after exposure to medical imaging ionizing radiation reduces the intracellular burden of radiation-induced DNA damage, thereby reducing the induction of radiation induced biological damage and the risk of future cancer. Genistein has substantial radioprotective effects linked to its strong antioxidant and anti-inflammatory properties, the ability to reduce the formation of chemical-induced DNA double strand breaks, and the ability to modulate the cell cycle and regulate signal transduction pathways.

The Active Agent

Genistein belongs to the pharmacological classes of soy isoflavone, flavonoid, polyphenol and phytoestrogen. It is also known as 5,7-dihydroxy-3-(4-hydroxyphenyl)-chromen-4-one (IUPAC), 5,7-dihydroxy-3-(4-hydroxyphenyl)-4H-1-benzopyran-4-one, 5,7,4'-trihydroxyisoflavone, 4',5,7-trihydroxyisoflavone, Genestein, Prunetol, Sophoricol and Differenol A. It has a Molecular Formula of $C_{15}H_{10}O_5$, a Molecular Weight of 270.237 g/mol (270.24 daltons), a Chemical Abstracts Service (CAS) Registry Number 446-72-0 and a Beilstein Registry Number 263823. It is commercially available from a number of sources, including DSM Nutritional Products, Inc. of Basel, Switzerland under Drug Master File (DMF) #19747-PND #104,709.

Administration

Administration Route

Genistein can be administered by virtually any of the commonly accepted practices for the administration of pharmaceutical preparations including specifically, but not exclusively, mucosal administration, oral consumption, ocular administration, subcutaneous injection, transdermal administration, intravascular administration, intramuscular administration, etc. Oral administration is generally preferred.

Mucosal administration of genistein includes such routes as buccal, endotracheal, nasal, pharyngeal, rectal, sublingual, vaginal, etc. For administration through the buccal/sublingual/pharyngeal/endotracheal mucosal, genistein may be formulated as an emulsion, gum, lozenge, spray, tablet or an inclusion complex such as cyclodextrin inclusion complexes. Nasal administration is conveniently conducted through the use of a sniffing powder or nasal spray. For rectal and vaginal administration genistein may be formulated as a cream, douche, enema or suppository.

Oral consumption of genistein may be effected by incorporating the genistein into a food or drink, or formulating the genistein into a chewable or swallowable tablet or capsule. The genistein is preferably orally administered as a nanosuspension in accordance with US Patent Application Publications 2012/0164190 and 2012/0121654, both hereby incorporated by reference.

Genistein is virtually insoluble in water, thereby limiting its bioavailability when administered orally. Genistein provided as a nanosuspension in accordance with US Patent Application Publications 2012/0164190 and 2012/0121654 has significantly improved bioavailability. This allows dosing without medical supervision, which enables pre-dosing at home prior to known and planned instances of medical imaging ionizing radiation exposure. To further improve oral bioavailability, genistein can also be incorporated as submicron size particles in an orally ingestible formulation. Generally, a dose of ~10 to 40 mg/kg of genistein provided as a nanosuspension should be effective for achieving the desired protective effect.

Ocular administration may be effected by incorporating genistein into a solution or suspension adapted for ocular application such as drops or sprays.

Subcutaneous, intravascular and intramuscular administration involves incorporating the genistein into a pharmaceutically acceptable and injectable carrier.

For transdermal administration, the genistein may be conveniently incorporated into a lipophilic carrier and formulated as a topical crème or adhesive patch.

Dose Rate

The range of dosages and dose rates effective for achieving the desired mitigation of detrimental effects from medical imaging ionizing radiation exposure may be determined in accordance with standard industry practices. The genistein may be administered prior to, during and/or after exposure to medical imaging ionizing radiation with a preference for administration both prior to and after such exposure. When administered prior to exposure, administration should be effected within forty eight hours, suitably within twenty four hours, preferably within eight hours, most preferably within four hours and ideally within two hours prior to exposure. When administered after exposure, administration should be effected within twelve hours, suitably within eight hours, preferably within four hours, most preferably within two hours and ideally within one hour after exposure.

The peak in DNA double strand breaks occurs within 30 min of radiation exposure. Generally, free genistein serum levels of between about 1-5 µM (~300-1400 ng/mL), measured in accordance with the procedure set forth in Prasain, J. K., Arabshahi, A, Moore, D. R., Greendale, G. A., Wyss, J. M., Barnes, S. (2010) *Simultaneous Determination of 11 Phytoestrogens in Human Serum Using a 2 min Liquid Cchromatography/Tandem Mass Spectrometry Method. J. Chromatogr. B,* 878, 994-1002 should be effective to mitigate cellular damage. It is preferred to achieve this effective range at the time of exposure, and maintain this level for at least 12 hours post exposure. We believe that one or more doses given within 24 hours prior to exposure and promptly after exposure will provide sustained serum levels of genistein within these desired levels.

We claim:

1. A method for mitigating long-term biological damage from exposure to low dose ionizing radiation comprising administration of genistein in the form of a nanosuspension to a mammal subject to exposure to 10 to 100 mGy ionizing radiation in an amount effective for achieving genistein serum levels of between 1-5 µM in the mammal throughout a time period from exposure to the ionizing radiation to twelve hours after exposure to the ionizing radiation.

2. A method for mitigating short-term biological damage from exposure to low dose ionizing radiation comprising administration of genistein in the form of a nanosuspension to a mammal subject to exposure to 10 to 100 mGy ionizing radiation in an amount effective for achieving genistein serum levels of between 1-5 µM in the mammal throughout a time period from exposure to the ionizing radiation to twelve hours after exposure to the ionizing radiation.

3. The method of claim 1 wherein the mitigated long-term detrimental effect is at least one of birth defect, cataract and cancer.

4. The method of claim 2 wherein the mitigated short-term detrimental effect is at least one of DNA double strand breaks and an increase in 8-hydroxy-2'-deoxyguanosine levels.

5. The method of claim 1 wherein the mammal is a human.

6. The method of claim 2 wherein the mammal is a human.

7. The method of claim 1 wherein administration is effected orally.

8. The method of claim 2 wherein administration is effected orally.

\* \* \* \* \*